US011235324B2

(12) United States Patent
Higgins et al.

(10) Patent No.: US 11,235,324 B2
(45) Date of Patent: Feb. 1, 2022

(54) TEMPERATURE-CYCLING MICROFLUIDIC DEVICES

(71) Applicant: Hewlett-Packard Development Company, L.P., Spring, TX (US)

(72) Inventors: Adam Higgins, Corvallis, OR (US); Alexander Govyadinov, Corvallis, OR (US); Michael W. Cumbie, Corvallis, OR (US)

(73) Assignee: Hewlett-Packard Development Company, L.P., Spring, TX (US)

( * ) Notice: Subject to any disclaimer, the term of this patent is extended or adjusted under 35 U.S.C. 154(b) by 163 days.

(21) Appl. No.: 16/643,954

(22) PCT Filed: Nov. 22, 2017

(86) PCT No.: PCT/US2017/063107
§ 371 (c)(1),
(2) Date: Mar. 3, 2020

(87) PCT Pub. No.: WO2019/103744
PCT Pub. Date: May 31, 2019

(65) Prior Publication Data
US 2021/0060548 A1 Mar. 4, 2021

(51) Int. Cl.
*B01L 3/00* (2006.01)
*B01L 7/00* (2006.01)
*C12Q 1/68* (2018.01)
(52) U.S. Cl.
CPC ............ *B01L 3/50273* (2013.01); *B01L 7/525* (2013.01); *C12Q 1/68* (2013.01); *B01L 2300/088* (2013.01);
(Continued)

(58) Field of Classification Search
CPC ..... B01L 2300/0816; B01L 2300/0867; B01L 2300/088; B01L 2300/1805;
(Continued)

(56) References Cited

U.S. PATENT DOCUMENTS 6,896,855 B1   5/2005 Kohler et al.
9,387,478 B2   7/2016 Bergstedt et al.
(Continued)

FOREIGN PATENT DOCUMENTS

WO   2007091230   8/2007
WO   2017119902   7/2017

OTHER PUBLICATIONS

Miralles et al., A Review of Heating and Temperature Control in Microfluidic Systems: Techniques and Applications, MDPI diagnostics, 10.3390/diagnostics3010033, 2013, 22 pages.
(Continued)

*Primary Examiner* — Jennifer Wecker
*Assistant Examiner* — Jonathan Bortoli
(74) *Attorney, Agent, or Firm* — Thorpe North & Western LLP

(57) ABSTRACT

The present disclosure is drawn to temperature-cycling microfluidic devices. In one example, a temperature-cycling microfluidic device can include a driver chip having a top surface and a heat exchange substrate having a top surface coplanar with the top surface of the driver chip. A fluid chamber can be located on the top surface of the driver chip. A first and second microfluidic loop can have fluid driving ends and fluid outlet ends connected to the fluid chamber and can include portions thereof located on the top surface of the heat exchange substrate. A first and second fluid actuator can be on the driver chip. The first and second fluid actuators can be associated with the fluid driving ends of the first and (Continued)

second microfluidic loops, respectively, to circulate fluid through the first and second microfluidic loops.

15 Claims, 10 Drawing Sheets

(52) U.S. Cl.
CPC .......... *B01L 2300/0816* (2013.01); *B01L 2300/0867* (2013.01); *B01L 2300/1805* (2013.01); *B01L 2300/1894* (2013.01); *B01L 2400/0442* (2013.01); *C12Q 2500/00* (2013.01); *C12Q 2563/159* (2013.01)

(58) Field of Classification Search
CPC ..... B01L 2300/1894; B01L 2400/0439; B01L 2400/0442; B01L 3/50273; B01L 7/525; C12Q 1/68; C12Q 2500/00; C12Q 2563/159
See application file for complete search history.

(56) References Cited

U.S. PATENT DOCUMENTS

| | | |
|---|---|---|
| 2004/0182564 A1 | 9/2004 | Tremmel |
| 2010/0267127 A1 | 10/2010 | Chung et al. |
| 2011/0220332 A1 | 9/2011 | Abenaim |
| 2015/0140645 A1* | 5/2015 | Davies .................. C12Q 1/686 435/287.2 |

OTHER PUBLICATIONS

Yuen et al., Microfluidic devices for fluidic circulation and mixing improve hybridization signal intensity on DNA arrays, Lab on a Chip, Biochemical Technologies, The Royal Society of Chemistry, DOI: 10.1039/b210274a, 2003, pp. 46-50.

International Search Report dated Aug. 30, 2018 for PCT/US2017/063107, Applicant Hewlett-Packard Development Company, L.P.

* cited by examiner

TEMPERATURE-CYCLING MICROFLUIDIC DEVICES

BACKGROUND

Microfluidics relates to the behavior, control and manipulation of fluids that are geometrically constrained to a small, typically sub-millimeter, scale. Microfluidics can be particularly useful for dealing with very small volume fluid samples, such as fluid samples of several microliters or less. For example, microfluidics can be used to manipulate biological samples, such as bodily fluids or sample fluids containing biological molecules such as proteins or DNA. These and a variety of applications for microfluidics exist, with various applications using differing controls over fluid flow, mixing, temperature, and so on.

BRIEF DESCRIPTION OF THE DRAWINGS

Additional features and advantages of the disclosure will be apparent from the detailed description which follows, taken in conjunction with the accompanying drawings, which together illustrate, by way of example, features of the present technology.

Figure 1:
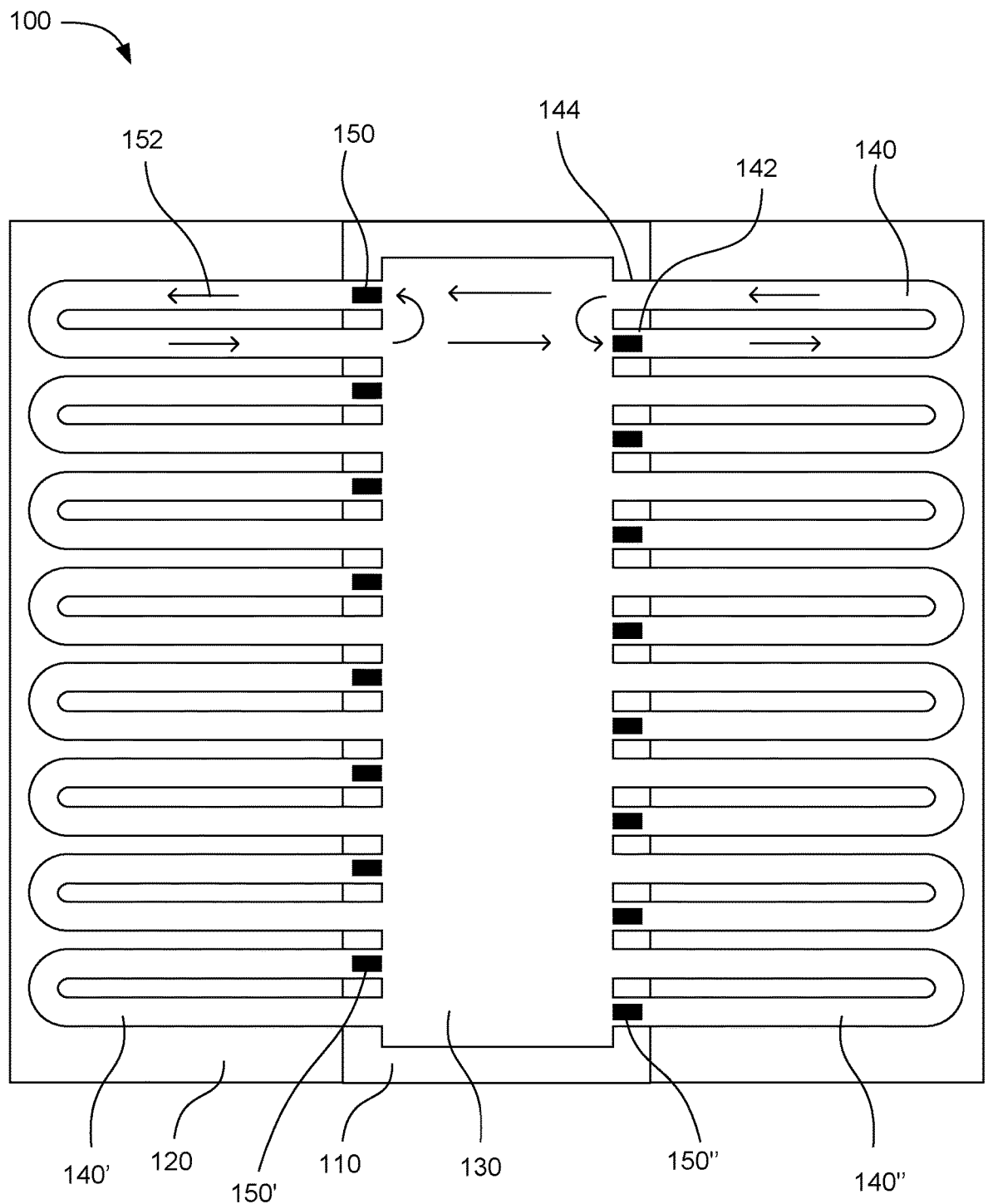
FIG. 1 is a schematic view of an example temperature-cycling microfluidic device in accordance with the present disclosure.

Reference will now be made to several examples that are illustrated herein, and specific language will be used herein to describe the same. It will nevertheless be understood that no limitation of the scope of the disclosure is thereby intended.

DETAILED DESCRIPTION

The present disclosure is drawn to temperature-cycling microfluidic devices and systems for heating and cooling fluids. The temperature-cycling microfluidic devices and systems described herein can be used to circulate a fluid sample through microfluidic loops. While the fluid is circulated, the fluid can undergo a temperature change. For example, the fluid can start at a relatively high temperature in the fluid chamber of the microfluidic device. The fluid can then be cooled to a lower temperature while the fluid is pumped through a microfluidic loop. When the fluid returns to the fluid chamber, the fluid can be heated to the higher temperature again. By continuously pumping fluid through the microfluidic loops, the temperature of fluid can be quickly and repeatedly cycled from the high temperature to the low temperature and back to the high temperature again.

The microfluidic devices described herein can be useful for any application that involves cycling the temperature of a fluid sample in a microfluidic loop. In a particular example, the microfluidic devices can be used for polymerase chain reaction (PCR) amplification of nucleic acids (DNA). PCR amplification can be used to generate thousands or millions of copies of a DNA molecule, starting with only one or a few DNA molecules. In this technique, a sample of fluid to be tested for DNA can be cyclically heated to a high temperature and cooled to a lower temperature. At the high temperature, the DNA molecule can be denatured by breaking hydrogen bonds between complementary bases in the DNA, yielding two single-stranded DNA molecules. At the low temperature, primers can be annealed to the single-stranded DNA molecules and DNA polymerize extends the new DNA strand by adding additional bases to the primers. In some cases, the annealing and elongation can be performed at two different temperatures. The temperature cycle can be repeated several times to create many new copies of the DNA molecule.

Processes have been developed for performed PCR amplification by flowing a fluid sequentially over multiple temperature-controlled zones. This allows the fluid to undergo a series of temperature cycles, while the temperature-controlled zone can maintain their temperatures at a steady state. These "continuous flow FOR" methods have often had several drawbacks. First, many of these methods have used a single channel through which the fluid flows. The channel may be serpentine shaped to save space in the amplification device, but using a single long channel for the fluid flow can still occupy a relatively large area and thus the amplification devices are relatively large. The number of temperature cycles can also be defined by the geometry of the channel, so there may be no easy way to adjust the number of temperature cycles used. Additionally, many such devices have included separate components for temperature control, DNA sensing, and fluid pumping.

The microfluidic devices described herein can make more efficient use of space by circulating the sample fluid through multiple microfluidic loops. Instead of using a long serpentine channel through with to flow the sample fluid, the fluid can be circulated through a shorter loop multiple times. When the fluid flows through the loop, the temperature of the fluid can be changed so that the fluid undergoes a temperature cycle every time the fluid circulates through the loop. The microfluidic devices can also include fluid actuators integrated in the device for pumping fluid through the microfluidic loops. Temperature sensors, heaters, and other sensors such as DNA sensors can also be integrated into the devices. Further, the microfluidic devices can also provide good mixing of the sample fluid, high rates of heat transfer to the sample fluid, and good temperature control.

In one example, a temperature-cycling microfluidic device can include a driver chip having a top surface and a heat exchange substrate having a top surface coplanar with the top surface of the driver chip. A fluid chamber can be located on the top surface of the driver chip. A first microfluidic loop can have a fluid driving end and a fluid outlet end connected to the fluid chamber. The first microfluidic loop can include a portion thereof located on the top surface of the heat exchange substrate. A first fluid actuator can be on the driver chip. The first fluid actuator can be associated with the fluid driving end of the first microfluidic loop to circulate fluid through the first microfluidic loop. A second microfluidic loop can also have a fluid driving end and a fluid outlet end connected to the fluid chamber. The second microfluidic loop can include a portion thereof located on the top surface of the heat exchange substrate. A second fluid actuator can be on the driver chip. The second fluid actuator can be associated with the fluid driving end of the second microfluidic loop to circulate fluid through the second microfluidic loop.

In certain examples, the heat exchange substrate can be a heat exchange chip formed at least partially from silicon. In further examples, the heat exchange chip can be separated from the driver chip by a substrate having a lower thermal conductivity than the heat exchange chip. In still further examples, the heat exchange chip can be to cool the fluid to a temperature lower than a temperature of the fluid chamber. In a particular example, the microfluidic device can also include an intermediate chip located between the driver chip and the heat exchange chip. The intermediate chip can be to heat the fluid to an intermediate temperature between the temperature of the heat exchange chip and the temperature of the fluid chamber.

In another example, the heat exchange chip can include a heater, a temperature sensor, a nucleic acid sensor, or a combination thereof. In a further example, the driver chip can include a heater, a temperature sensor, a nucleic acid sensor, or a combination thereof.

In some examples, the first and second microfluidic loops can include multiple turns over the heat exchange substrate.

In certain examples, the fluid actuators can be thermal resistors or piezoelectric elements.

In a further example, a temperature-cycling microfluidic device can include a driver chip, a heat exchange chip having a top surface coplanar with the top surface of the driver chip, a fluid chamber on the top surface of the driver chip, and a first microfluidic loop including a first heat exchange chamber over the heat exchange chip. The first microfluidic loop can have a fluid driving end and a fluid outlet end connected to the fluid chamber. The first heat exchange chamber can have a greater chamber height than a remainder of the first microfluidic loop. A first fluid actuator can be located on the driver chip and associated with the fluid driving end of the first microfluidic loop to circulate fluid through the first microfluidic loop. A second microfluidic loop can also have a fluid driving end and a fluid outlet end connected to the fluid chamber. The second microfluidic loop can include a second heat exchange chamber over the heat exchange chip. The second heat exchange chamber can also have a greater chamber height than a remainder of the second microfluidic loop. A second fluid actuator can be located on the driver chip and associated with the fluid driving end of the second microfluidic loop to circulate fluid through the second microfluidic loop.

In further examples, the first and second microfluidic loops can also include additional heat exchange chambers located over the driver chip.

In another example, a system for heating and cooling a fluid can include a temperature-cycling microfluidic device and a reading device. The temperature-cycling microfluidic device can include a driver chip and a heat exchange chip coplanar with the driver chip and separated from the driver chip by a substrate. The driver chip can include a temperature sensor, a heater, and an electrical interface electrically connected to the temperature sensor and heater. The heat exchange chip can also include a temperature sensor, a heater, and an electrical interface connected to the temperature sensor and heater. A fluid chamber can be located over the driver chip. Multiple microfluidic loops can have a fluid driving end and a fluid outlet end connected to the fluid chamber. The individual microfluidic loops can include a portion thereof located on the heat exchange chip. Multiple fluid actuators can be on the driver chip. Individual fluid actuators can be associated with the fluid driving end of individual microfluidic loops to circulate fluid through the microfluidic loops. The reading device can include electrical interfaces to connect to the electrical interfaces of the driver chip and the heat exchange chip. The reading device can include a processor to driver the fluid actuators, measure temperatures using the temperature sensors, and heat the driver chip and heat exchange chip to control the temperature of the chips within a temperature range.

In one example, the heat exchange chip can be to cool the fluid to a lower temperature than the driver chip.

In another example, the substrate can have a lower thermal conductivity than the heat exchange chip.

In a further example, the microfluidic device can include an intermediate located between the driver chip and the heat exchange chip. The intermediate chip can be to heat the fluid to an intermediate temperature between the temperature of the heat exchange chip and the temperature of the fluid chamber. In a particular example, the intermediate chip can include a temperature sensor, a heater, and an electrical interface electrically connected to the temperature sensor and heater.

In some examples, a sample fluid can be loaded into a fluid chamber that can be located over a driver chip. Microfluidic loops can connect at both ends to the fluid chamber. As used herein, "microfluidic loops" refers to structures that can hold very small volumes of fluid, such as from a fraction of a picoliter to several microliters. Additionally, "microfluidic loops" are referred to as "loops" because they have two ends that connect to the same fluid chamber. In some examples, the device can include at least a first microfluidic loop and a second microfluidic loop. The microfluidic loops can extend off of the driver chip and onto a heat exchange substrate. The driver chip can include fluid actuators for pumping fluid through the microfluidic loops. When the driver chip and the heat exchange substrate are maintained at different temperatures, the fluid can cycle between the two temperatures every time the fluid flows around the microfluidic loops.

In certain examples, the microfluidic device can include a first microfluidic loop and a second microfluidic loop. A first fluid actuator and a second fluid actuator can be associated with the first and second microfluidic loops to pump fluid through the first and second microfluidic loops, respectively. Although microfluidic loops and fluid actuators may be referred to herein as "first" and "second," no limitation is implied on the location or order of these components. In further examples, the microfluidic device can include more than two microfluidic loops. In some examples, the microfluidic device can include 4 microfluidic loops, 8 microfluidic loops, 10 microfluidic loops, 16 microfluidic loops, 20 microfluidic loops, and so on. In various other examples, the microfluidic device can include from 2 to 100 microfluidic loops, or even more than 100 microfluidic loops in some cases. In some examples, fluid actuators can be associated with some or all of the microfluidic loops. For example, individual microfluidic loops can have a fluid actuator at a fluid driving end of the microfluidic loop. As used herein, "multiple microfluidic loops" refers to at least two microfluidic loops, and can encompass any number of microfluidic loops two or greater. Similarly, "multple fluid actuators" refers to any number of fluid actuators two or greater.

FIG. 1 shows one example of a temperature-cycling microfluidic device 100 according to the present disclosure. The microfluidic device includes a driver chip 110 and a heat exchange substrate 120. The heat exchange substrate can have a top surface that can be coplanar with the top surface of the driver chip. A fluid chamber 130 can be located on the top surface of the driver chip. Multiple microfluidic loops 140 connect to the fluid chamber at a fluid driving end 142 and a fluid outlet end 144. The multiple microfluidic loops can include a first microfluidic loop 140', a second microfluidic loop 140", as well as additional microfluidic loops. The microfluidic loops extend from the fluid chamber, off of the driver chip and onto the heat exchange substrate. Multiple fluid actuators 150 are on the driver chip. The multiple fluid actuators can include a first fluid actuator 150', a second fluid actuator 150", as well as additional fluid actuators. Individual fluid actuators are associated with the fluid driving end of individual microfluidic loops to circulate fluid through the microfluidic loops. In this example, the fluid actuators are distributed along opposite sides of the fluid chamber in a staggered fashion to increase mixing of the fluid. The fluid can flow throughout the device as shown by flow arrows 152. The fluid can flow through the microfluidic loops and back into the fluid chamber. When the fluid re-enters the fluid chamber, some of the fluid can circulate back to the same microfluidic loop again, and some of the fluid can travel across the fluid chamber to be pumped into a different microfluidic loop. Mixing the fluid in this way can overcome diffusion limitations, increase chemical reaction rates, and increase heat transfer to the fluid.

In some examples, the fluid in the fluid chamber can be maintained at a high relative temperature and then the fluid can be cooled to a low relative temperature when the fluid flows around the microfluidic loops. For example, in the device shown in FIG. 1, the fluid in the fluid chamber can be heated to temperature above ambient temperature by the driver chip. The heat exchange substrate can be a material that can be exposed to ambient temperature, so that the fluid naturally cools toward ambient temperature while the fluid is in the microfluidic loops. When the fluid re-enters the fluid chamber, the fluid can be reheated to the higher temperature again. This example can take advantage of passive cooling by the heat exchange substrate at ambient temperature. The driver chip can in some cases include a heater such as a resistive heater formed on the driver chip. In other examples, the fluid actuators can be thermal resistors that can also contribute to heating the fluid. In such an example, the driver chip may also include a temperature sensor so that the temperature of the fluid over the driver chip can be measured and controlled. The low temperature reached by the fluid while circulating through the microfluidic loops can be controlled by adjusting the speed at which the fluid is pumped through the microfluidic loops. For example, if the low temperature is desired to be close to ambient temperature, then a slow pumping speed can be used so that the fluid has time to approach the ambient temperature in the microfluidic loops. If a higher temperature is desired, then the pumping speed can be increased so that the fluid does not cool down as much when circulating through the microfluidic loops. In some examples, additional temperature sensors can be located in or near the microfluidic loops to provide feedback on the temperature of the fluid in the microfluidic loops.

In a specific example, the device shown in FIG. 1 can be used for PCR amplification. In this case, the fluid chamber can be maintained at a high temperature for denaturing DNA molecules in the fluid. The fluid can then cool to a lower temperature for annealing of primers and elongation of new DNA molecules in the microfluidic loops. For example, the fluid chamber can be maintained at a high relative temperature from 80° C. to 103° C. and the fluid can be cooled to a low relative temperature from 48° C. to 82° C. when flowing through the microfluidic loops. The desired low relative temperature can be achieved by pumping the fluid through the microfluidic loops at an appropriate flow rate to allow the ambient temperature heat exchange substrate to cool the fluid down to the desired temperature. In another example, the driver chip can be heated to a slightly higher temperature than the targeted high relative temperature to ensure that the fluid in the fluid chamber reaches the high relative temperature. For example, the if the target high relative temperature is 95° C. then the driver chip can be heated to from about 96° C. to about 99° C. In other examples, the driver chip can be heated to from about 1° C. to about 4° C. over the target high relative temperature.

In addition to PCR tests, the microfluidic devices described herein can be used to perform a variety of other tests. Non-limiting examples of other tests that can be performed using the microfluidic devices described herein can include enzyme-linked immunoabsorbent assay (ELISA) immunoassay testing, isothermal amplification such as multiple displacement amplification (MDA), loop-mediated isothermal amplification (LAMP), rolling circle amplification (RCA), helicase-dependent amplification (HAD), recombinase polymerase amplification (RPA), nucleic acid sequence-based amplification (NASBA), hematology testing, and so on. A variety of other biochemical and non-biochemical tests can also benefit from the enhanced mixing and temperature control provided by the microfluidic devices described herein.

Figure 2:
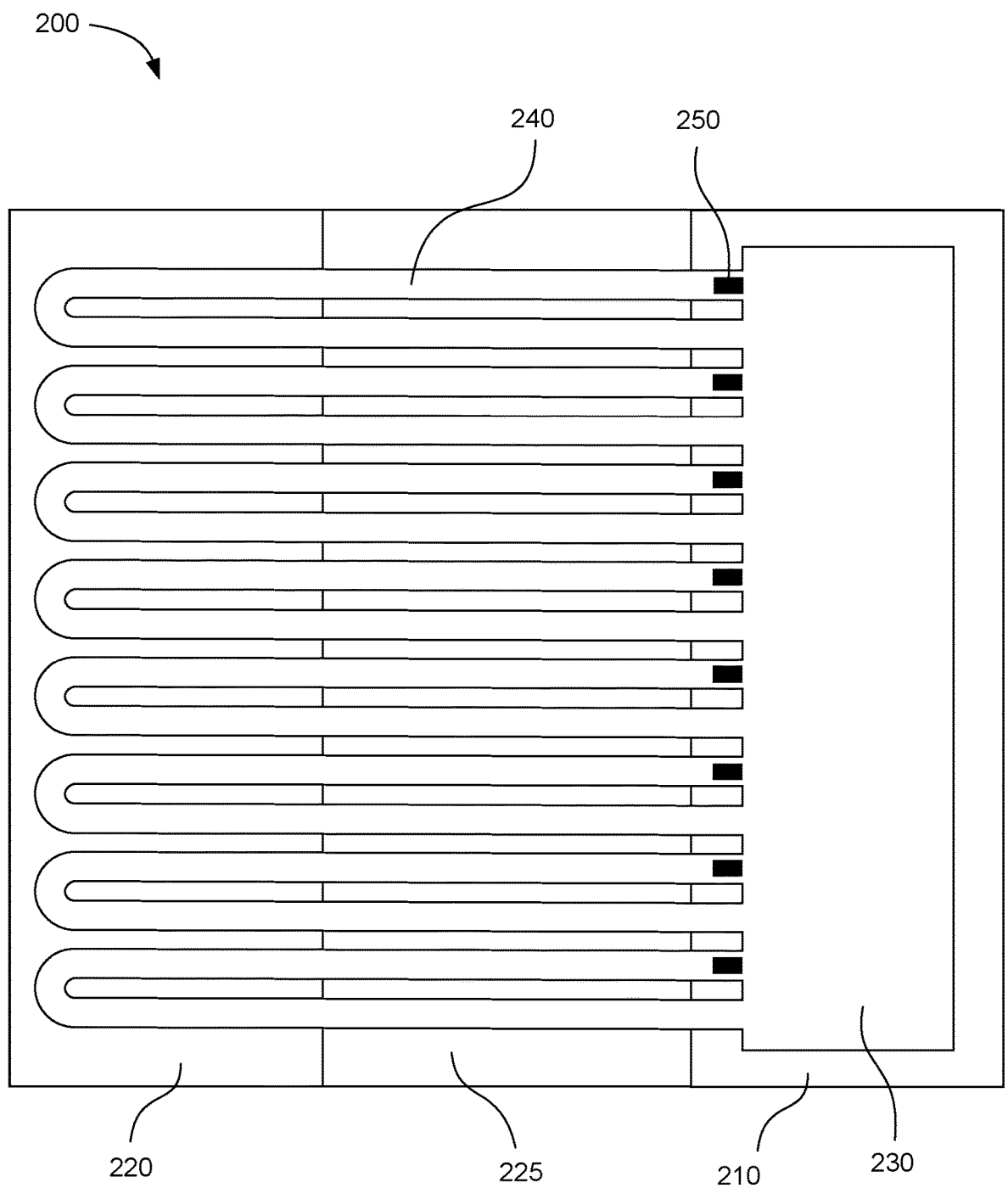
FIG. 2 is a schematic view of another example temperature-cycling microfluidic device in accordance with the present disclosure.

Even better temperature control can be achieved by using additional heat exchange chips with active temperature control. Instead of relying on a substrate at ambient temperature, additional heat exchange chips can include additional temperature sensors and additional heaters to maintain the heat exchange chips at a particular temperature. FIG. 2 shows one such example temperature-cycling microfluidic device 200. The device includes a driver chip 210 and a heat exchange chip 220. The heat exchange chip can have a top surface that can be coplanar with the top surface of the driver chip. The heat exchange chip can be separated from the driver chip by a substrate 225. A fluid chamber 230 can be located over the driver chip. Multiple microfluidic loops 240 connect to the fluid chamber and extend across the substrate to the heat exchange chip. Multiple fluid actuators 250 are associated with fluid driving ends of the microfluidic loops to circulate fluid through the microfluidic loops.

In some examples, the heat exchange chip can be separated from the driver chip by a substrate that has a lower thermal conductivity than the heat exchange chip. The temperature of the fluid circulating through the microfluidic loops can remain relatively constant when the fluid is over the substrate, and then the change more quickly when the fluid is over the heat exchange chip. In some examples, the heat exchange chip can be formed at least partially of silicon. The substrate can be formed of another material that has a lower thermal conductivity than silicon. Non-limiting examples of substrate materials can include polycarbonate, glass filled epoxy, polyacrylic glass, polymethacrylate, polymethylmethacrylate glass, polypropylene, polyamide/nylon or any other high glass transition temperature plastic.

In various examples, the driver chip can include the multiple fluid actuators for pumping fluid through the microfluidic loops. In some examples, the fluid actuators can be a thermal resistor or a piezoelectric element. These actuators can be used to displace fluid, either by boiling the fluid to form a bubble in the case of thermal resistors, or by moving a piezoelectric element. The fluid actuator can be located in a microfluidic loop in a location that is asymmetric with respect to the length of the microfluidic channel. In other words, the fluid actuator can be located closer to one end of the microfluidic loop than to the other. In certain examples, the fluid actuators can be located at or near the fluid driving end of a microfluidic loop. When the fluid actuator repeatedly displaces fluid, a net flow can be produced in one direction. For example, repeatedly forming bubbles using a thermal resistor can displace fluid into the microfluidic loop and produce a net flow of fluid from the fluid driving end of the microfluidic loop to the fluid outlet end of the microfluidic loop.

The fluid actuators can be formed on the driver chip by any suitable method, such as patterning resistors or piezoelectric elements on a surface of the driver chip. Other electronic components can also be formed on the driver chip, such as heaters, temperature sensors, and sensors for detecting a species in the sample fluid such as a DNA sensor. In some examples, the driver chip can also include electronics for powering and controlling the fluid actuators, heaters, and sensors. In further examples, a power source and control electronics can be in a separate device, and the driver chip can include an electrical interface that can connect to the separate device. In some examples, this arrangement can allow for a lower cost microfluidic testing device that can be disposable, with a separate reusable device for powering and controlling the fluid actuators, heaters, and sensors.

Figure 3A:
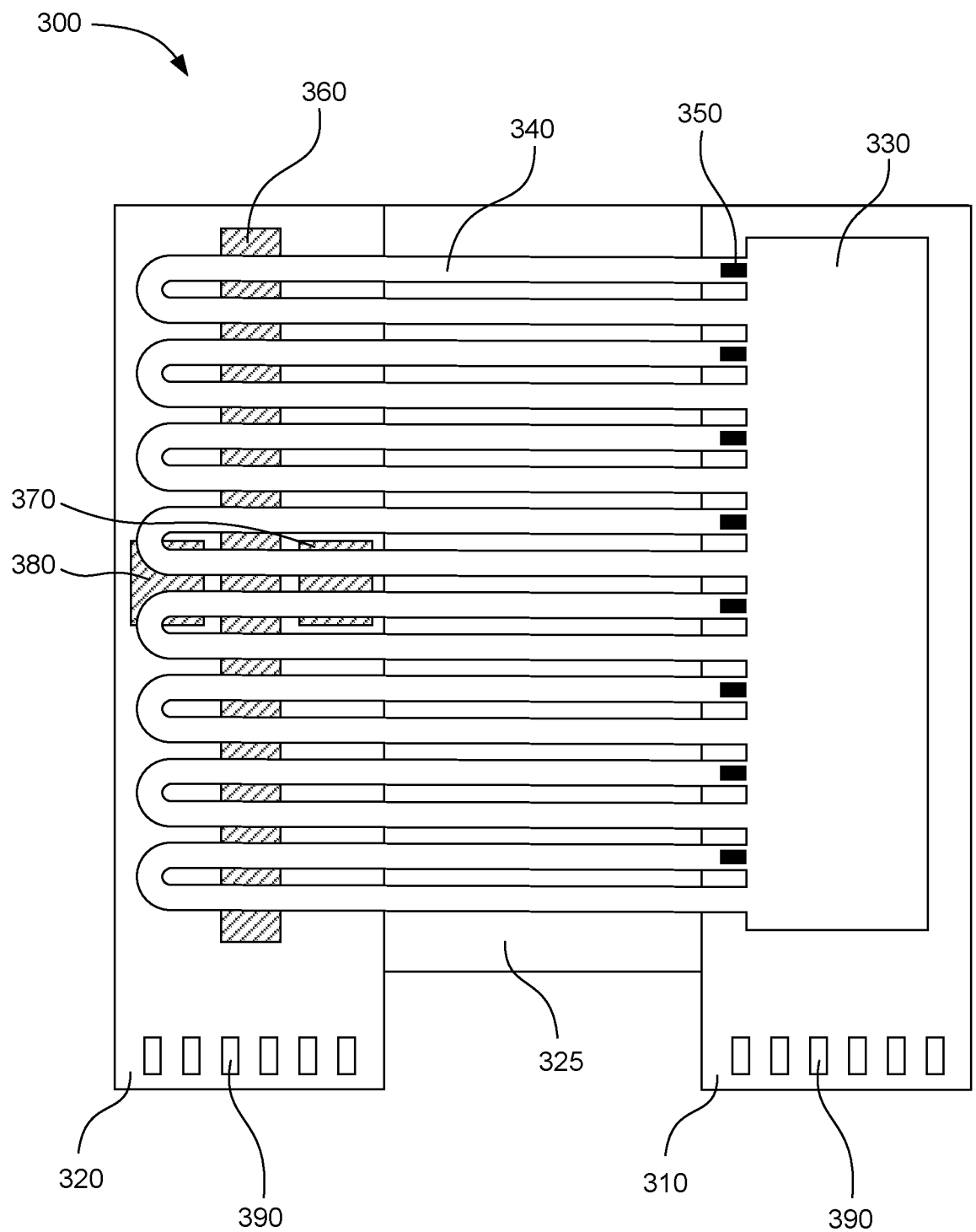
FIG. 3A is a top plan schematic view of an example temperature-cycling microfluidic device in accordance with the present disclosure.

In further examples, the heat exchange chip can include electronic components such as a resistive heater, a temperature sensor, or a sensor for detecting a particular species in the fluid sample such as a DNA sensor. FIG. 3A is a top plan view of an example temperature-cycling microfluidic device 300 including such electronic components. This device also includes a driver chip 310 and a heat exchange chip 320 separated from the driver chip by a substrate 325. A fluid chamber 330 is located over the driver chip. Multiple microfluidic loops 340 connect to the fluid chamber and extend off of the driver chip and over the heat exchange chip. Multiple fluid actuators 350 are associated with fluid driving ends of the individual microfluidic loops to circulate fluid around the microfluidic loops. In this example, the heat exchange chip also includes a heater 360 located under the microfluidic loops to transfer heat to or from the fluid in the microfluidic loops. A temperature sensor 370 on the heat exchange chip can measure the temperature of the heat exchange chip. A DNA sensor 380 on the heat exchange chip can detect the presence of amplified DNA in the sample fluid. The heat exchange chip and driver chip can also include electrical interfaces 390. The electrical interface of the heat exchange chip can be electrically connected to the heater, temperature sensor, and DNA sensor through electrical traces (not shown). The electrical interface of the driver chip can be electrically connected to the fluid actuators through electrical traces (also not shown). In further examples, the driver chip can also include a heater, temperature sensor, DNA sensor, or a combination thereof.

These additional electronic components can also be connected to the electrical interface. The electrical interfaces can allow a separate reading device to power and control the components on the driver chip and heat exchange chip.

In various examples, a variety of temperatures can be used as target temperatures for the driver chip and heat exchange chip. In some examples, the driver chip can be maintained at a high relative temperature while the heat exchange chip can be maintained at a low relative temperature. In other examples, the heat exchange chip can be at a high relative temperature and the driver chip can be at a low relative temperature. In the specific case of PCR amplification, the chip at the high relative temperature can be the location where DNA denaturation occurs, while the chip at the low relative temperature can be the location where annealing and elongation occurs. Because the temperature ranges for annealing and elongation are typically above ambient temperature, the chip that is at the annealing and elongation temperature can include a heater to keep the chip at the correct temperature. Thus, even though the chip includes a heater, the chip can actually act as a heat sink to cool the fluid over the chip down from the denaturation temperature to the annealing and elongation temperature.

The driver chip and heat exchange chip can be maintained at a target temperature using heaters and temperature sensors on the chips. As mentioned above, in some examples the driver chip and heat exchange chip can include electrical interfaces that connect to a separate reading device. The reading device can include a processor to read temperature data from the temperature sensors and supply sufficient power to the heaters to maintain the temperatures of the chips at the target temperatures. In other examples, the processor for controlling the temperature of the chips can be located on the chips themselves. In either example, the processor can control the temperature through the use of a process control loop such as a PID loop.

In further examples, the driver chip and/or heat exchange chip can include a sensor for sensing the presence of a particular species in the sample fluid. In the case of DNA sensors, an example sensor may be an optical sensor for detecting the presence of DNA molecules in the sample fluid. In a specific example, an optical sensor can detect fluorescence of a dye (also present in the sample fluid) that intercalates in the double-stranded DNA. Optical sensors can also be used with hydrolysis probes, which are fluorescent dyes that can be released from primers embedded in copied DNA strands. In some examples, optical sensors can include a light source such as an LED. In particular, a blue LED can be used as the light source. The optical sensor can also include a photodetector with a high path filter to attenuate 3-6 orders of magnitude the exciting blue light. In further examples, electrochemical DNA sensors can be used. In certain examples, electrochemical sensors can produce an electrical signal in response to redox intercalating dye reacting with amplified DNA. In other examples, electrochemical sensors can selectively detect $H^+$ ions produced as a byproduct of DNA amplification. Ion sensitive field effect transistor (ISFET) sensors can be used for this purpose. Further examples of sensors can include microbalance and microcantilever sensors. In many examples, these sensors can be integrated into the driver chip or another chip in the microfluidic device. In some examples, the DNA sensor can be on the chip that is maintained at the lower temperature for annealing and elongation, so that the DNA sensor can detect fully formed chains of amplified DNA.

In further examples, the fluid chamber can be located over the driver chip. In certain examples, the driver chip itself can be the floor of the fluid chamber such that the fluid is in direct contact with the driver chip and the electronic components on the driver chip. In other examples, a thin layer of material can be deposited over the driver chip to protect components on the driver chip exposure to fluid. In such examples, the floor of the fluid chamber can be a thin layer of another material deposited over the driver chip. The thickness of this layer can be small to maximize heat transfer from the driver chip to the fluid in the fluid chamber. In some examples, the floor of the fluid chamber can be a layer of material that is from 1 µm to 200 µm thick. In certain examples, the material can be a photoimageable epoxy such as SU-8.

Figure 3B:
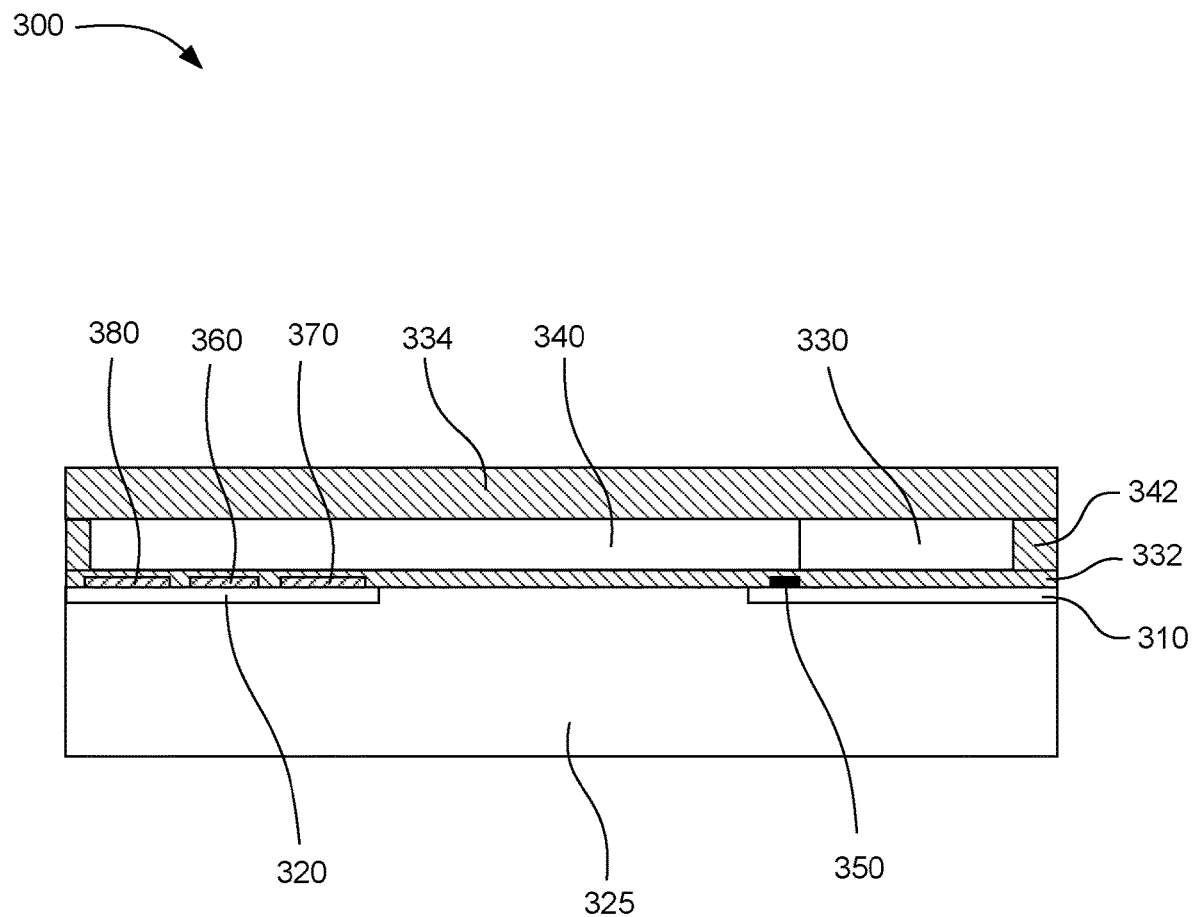
FIG. 3B is a side cross-sectional view of the example temperature-cycling microfluidic device shown in FIG. 3A.

FIG. 3B shows a cross-sectional side view of the microfluidic device 300 shown in FIG. 3A, to clarify the structure of the device. The driver chip 310 and heat exchange chip 320 are embedded in substrate 325, so that the chips and the substrate between the chips have a co-planar top surface. Fluid actuators 350 are located on the surface of the driver chip. The heater 360, the temperature sensor 370, and the DNA sensor 380 are located on the surface of the heat exchange chip. A thin floor layer 332 is then deposited over the chips and substrate. A microfluidic layer 342 is deposited over the floor layer to define the fluid chamber 330 and microfluidic loops 340. Finally, a ceiling layer 334 is deposited over the microfluidic layer.

In some examples, the fluid chamber can hold a volume of fluid from 3 pL to 2 µL. In certain examples, the fluid chamber can have a length of 50 µm to 10,000 µm, a width of 5 µm to 1,000 µm, and a height of 9 µm to 500 µm. In some cases, the height of the fluid chamber can be the same height as the microfluidic loops or channels that connect to the fluid chamber. In further examples, the microfluidic loops can account for a majority of the total fluid volume of the device. Thus, while the fluid chamber may hold a volume of from 3 pL to 2 µL, the total volume of fluid accommodated by the device may be from 6 pL to 40 µL or more.

In certain examples, the fluid chamber can have a ceiling with an opening for filling fluid into the chamber. In one example, the entire top of the fluid chamber can be open for filling fluid into the chamber. In another example, a majority of the fluid chamber can be closed by a ceiling, and a relatively small aperture can be located anywhere on the ceiling to allow for filling fluid into the chamber. Alternatively, an aperture can be formed in the driver chip and floor of the fluid chamber so that fluid can be filled into the fluid chamber through the driver chip. In a further example, the device can include a filling opening at another location and a microfluidic channel connecting the filling opening to the fluid chamber.

Microfluidic loops can extend off of the driver chip and onto a heat exchange substrate such as a heat exchange chip in some examples. In certain examples, the microfluidic loops can have a length from 50 µm to 10 mm. In some examples, from 80% to 100% of the length of the microfluidic loops can be located outside the boundaries of the driver chip. In further examples, from 90% to 99% of the length of the microfluidic loops can be located outside the boundaries of the driver chip. In further examples, the ratio of total fluid volume located outside the boundary of the driver chip to the total fluid volume over the driver chip can be from 2:1 to 20:1. The total fluid volume over the driver chip can include both fluid in the fluid chamber and fluid in any portions of the microfluidic loops that are over the driver chip. In several examples, the small portion of the microfluidic loops can be over the driver chip so that the fluid actuators formed on the driver chip can be located within the microfluidic loops.

Additionally, in some examples the portions of the microfluidic loops that are outside the boundaries of the driver chip and heat exchange chip can be supported by a substrate that is less thermally conductive. For example, in one example the driver chip and heat exchange chip in the device can include silicon, and the substrate supporting the portion of the microfluidic loops can be a material other than silicon. In certain examples, the substrate can be a polymer, a photoimageable epoxy such as Su-8, glass, or another material.

In some examples, the microfluidic loops can have a cross-sectional area from 45 µm$^2$ to 500,000 µm$^2$. In certain examples, the microfluidic loops can have a rectangular cross section with a cross section width from 5 µm to 1,000 µm and a cross section height from 9 µm to 500 µm. In one example, the microfluidic loops can have the same height as the fluid chamber.

The microfluidic devices described are not limited to being formed by any particular process. However, in some examples, any of the microfluidic devices described herein can be formed from multiple layers as shown in FIG. 3B. In certain examples, the layers can be formed photolithographically using a photoresist. In one such example, the layers can be formed from an epoxy-based photoresist such as SU-8 or SU-8 2000 photoresist, which are epoxy-based negative photoresists. Specifically, SU-8 and SU-8 2000 are Bisphenol A Novolac epoxy-based photoresists that are available from various sources, including MicroChem Corp. These materials can be exposed to UV light to become crosslinked, while portions that are unexposed remain soluble in a solvent and can be washed away to leave voids.

In some examples, the temperature of the fluid can more closely approach the temperature of the driver chip or heat exchange chip over which the fluid is flowing when the fluid has a long residence time over the respective chip. Longer residence times can be achieved, in some cases, by decreasing the flow rate of fluid through the microfluidic loops. In other examples, the geometry of the microfluidic loops can be designed to provide for a longer residence time over the chip. For example, the microfluidic loops can have a longer length located over one of the chips, with multiple turns over the chip, a larger surface area over the chip, or a larger volume chamber located over the chip.

Figure 4:
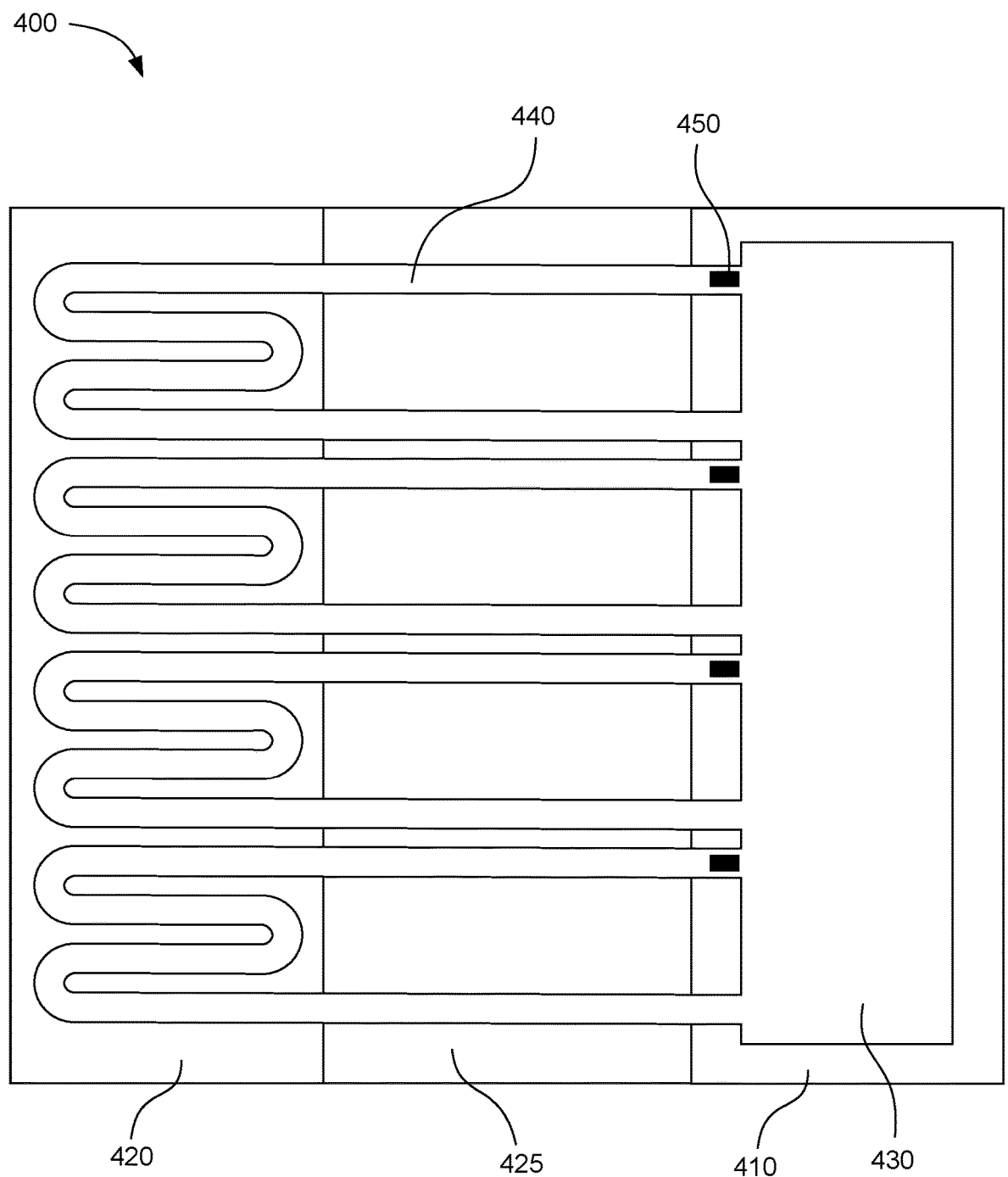
FIG. 4 is a schematic view of another example temperature-cycling microfluidic device in accordance with the present disclosure.

FIG. 4 shows an example temperature-cycling microfluidic device 400 that can increase residence time of the fluid over the heat exchange chip 420. The device includes a driver chip 410 separated from the heat exchange chip by a substrate 425, a fluid chamber 430 over the driver chip, multiple microfluidic loops 440 connected to the fluid chamber, and multiple fluid actuators 450 associated with fluid driving ends of the individual microfluidic loops. In this example, the microfluidic loops include three turns over the heat exchange chip. Because of these turns, fluid in the microfluidic loop can travel over the heat exchange chip for a longer period of time, allowing the temperature of the fluid to approach closer to the temperature of the heat exchange chip. The longer residence time over heat exchange chip can also allow more time for chemical reactions to occur at the temperature of the heat exchange chip. In some examples, the temperature of the fluid can stay nearly constant as the fluid flows back from the heat exchange chip toward the fluid chamber. Therefore, chemical reactions that occur at the temperature of the heat exchange chip can continue to occur in the fluid while the fluid flows through the last leg of the microfluidic loop returning to the fluid chamber.

Because the temperature of fluid in the microfluidic loop may approach the temperature of the heat exchange chip, but not necessarily reach the exact temperature of the heat exchange chip, in some cases the heat exchange chip can be held at a slightly lower or higher temperature than the target temperature for the fluid in the microfluidic loop. For examples, if the heat exchange chip is at a low relative temperature and the driver chip is at a high relative temperature, the heat exchange chip can be held at a temperature that is about 1° C. to about 4° C. below the target temperature for the fluid. In another example, the heat exchange chip can be at a high relative temperature and driver chip can be at a low relative temperature. In this example, the heat exchange chip can be held at a temperature that is about 1° C. to about 4° C. higher than the target temperature of the fluid. Similarly, the driver chip can be held at a temperature that is about 1° C. to about 4° C. higher or lower than the target temperature for the fluid in the fluid chamber. When multiple turns are used, in some examples the difference between the chip temperature and the target temperature can be smaller compared to examples where only a single turn is used, because the fluid can have a longer residence time over the chip to closer approach the temperature of the chip.

Figure 5:
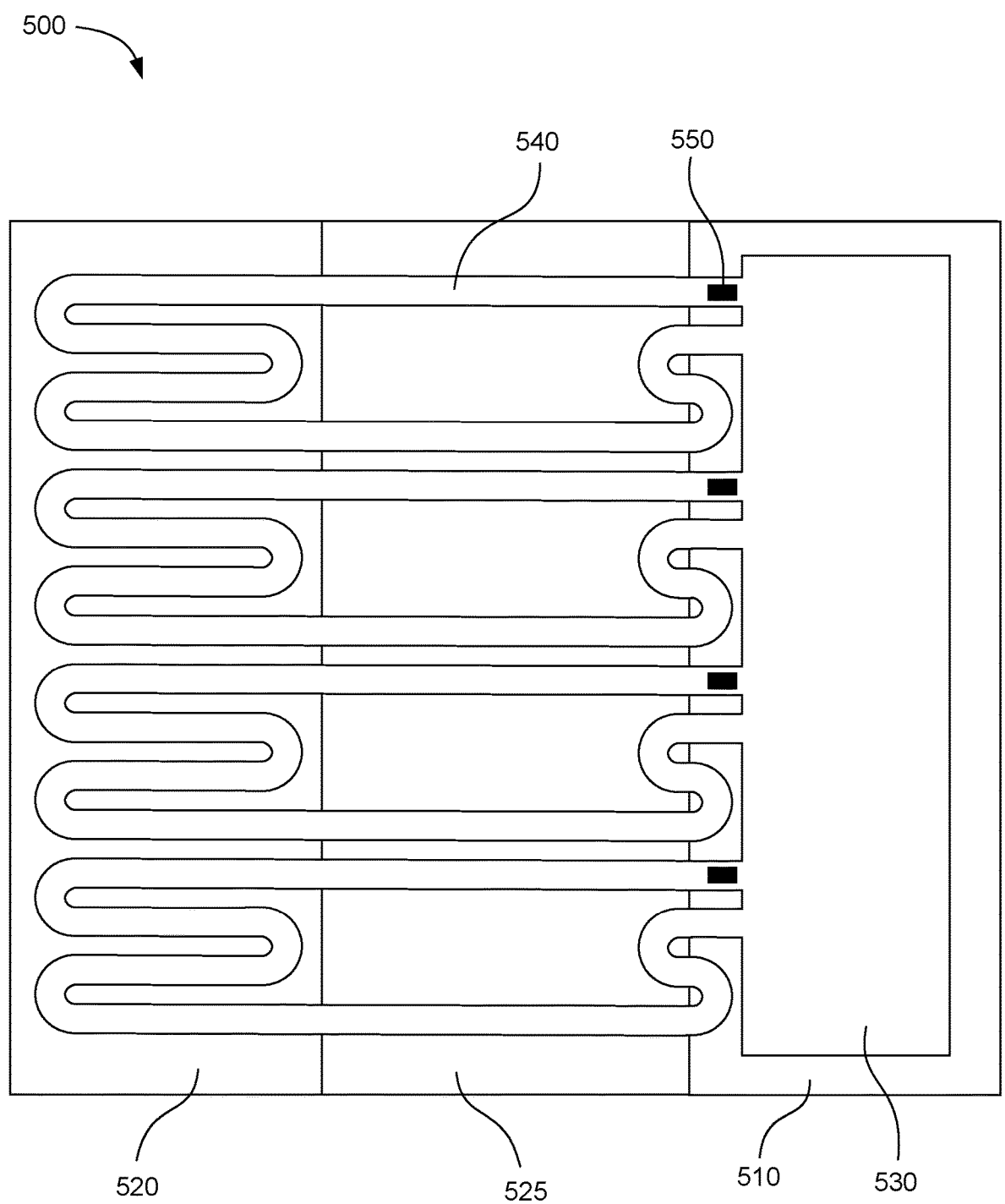
FIG. 5 is a schematic view of another example temperature-cycling microfluidic device in accordance with the present disclosure.

FIG. 5 shows another example temperature-cycling microfluidic device 500 that includes multiple turns. Again, this example includes a driver chip 510, a heat exchange chip 520 separated from the driver by a substrate 525, a fluid chamber 530 over the driver chip, multiple microfluidic loops 540 connected to the fluid chamber, and multiple fluid actuators 550 at the fluid driving ends of the individual microfluidic loops. In this example, the microfluidic loops include three turns over the heat exchange chip, and two additional turns over the driver chip before the microfluidic loops connect back to the fluid chamber. The fluid flowing through the microfluidic loops in this example can have more time over the heat exchange chip as well as extra time to approach the driver chip temperature before flowing back into the fluid chamber.

Figure 6:
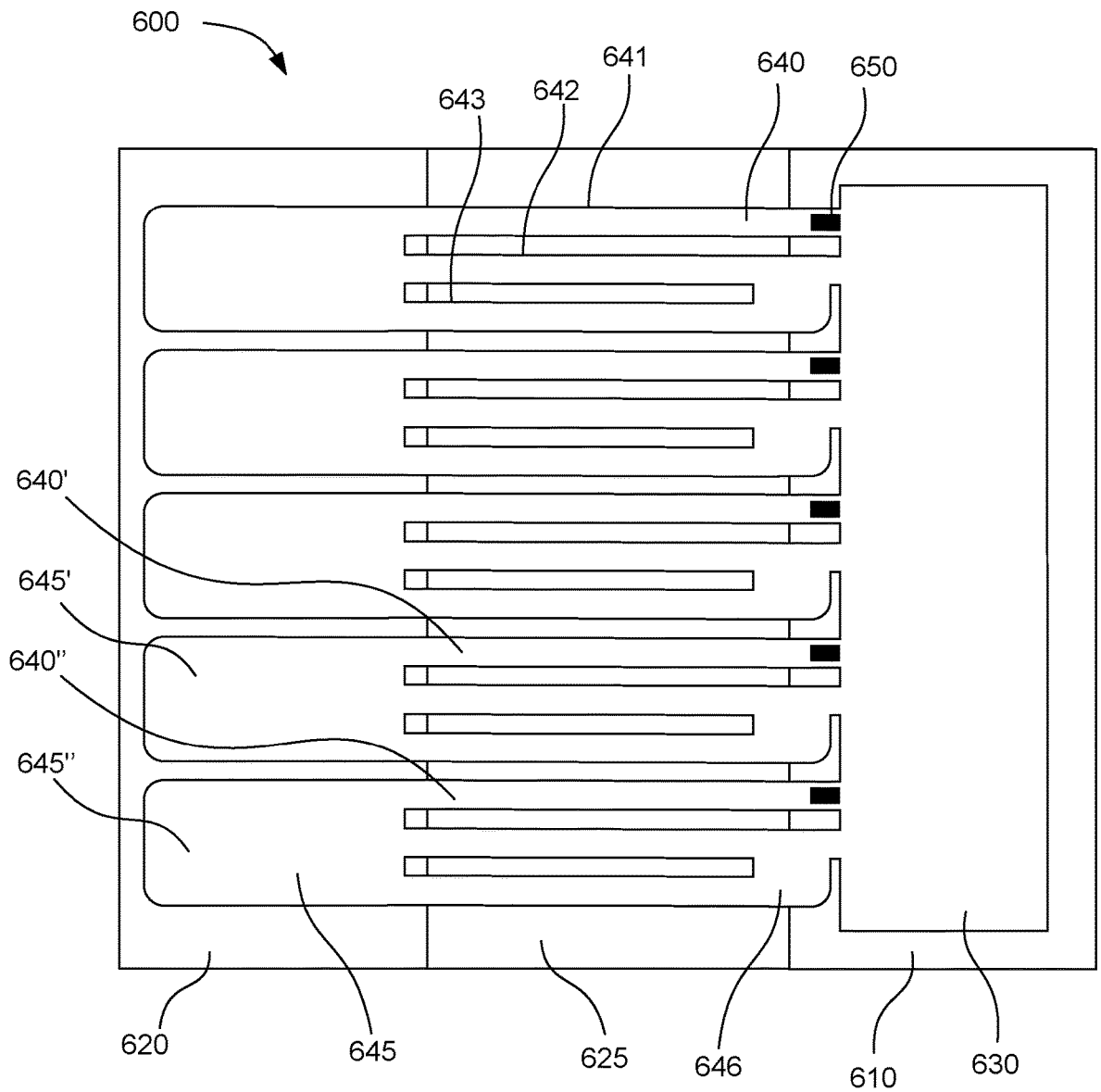
FIG. 6 is a schematic view of yet another example temperature-cycling microfluidic device in accordance with the present disclosure.

FIG. 6 shows another example temperature-cycling microfluidic device 600. This example includes a driver chip 610, a heat exchange chip 620 separated from the driver by a substrate 625, a fluid chamber 630 over the driver chip, multiple microfluidic loops 640 connected to the fluid chamber, and multiple fluid actuators 650 at the fluid driving ends of the individual microfluidic loops. The microfluidic loops in this example include a first microfluidic loop 640' with a first heat exchange chamber 645' located over the heat exchange chip, and a second microfluidic loop 640" with a second heat exchange chamber 645". Fluid can be driven by a fluid actuator through a first leg 641 of a microfluidic loop to the heat exchange chamber. The heat exchange chamber can have a larger volume compared to the interior volume of a microfluidic loop without such a heat exchange chamber. Therefore, the fluid can have a longer residence time over the heat exchange chip while the fluid is inside this heat exchange chamber. Fluid can then flow out of the heat exchange chamber through two returning legs 642, 643 of the microfluidic loop. Because there are two returning legs of the microfluidic loop, the flow rate of fluid through the individual return legs can be half the flow rate of the fluid through the first leg of the microfluidic loop. This can allow more time for chemical reactions to take place at the temperature of the heat exchange chip. The first and second microfluidic loops in this example also include additional heat exchange chambers 646 located over the driver chip. The additional heat exchange chambers can provide additional time for the fluid to approach the temperature of the driver chip before the fluid flows back into the fluid chamber.

In certain examples, the heat exchange chambers can have a greater chamber height than the remainder of the microfluidic loops. This can provide an even greater volume compared to microfluidic loops without such heat exchange chambers. This can allow the fluid more residence time inside the heat exchange chamber. In some examples, a larger volume chamber can also be useful for detection of specific species in the fluid. For example, some DNA sensors such as optically-based sensors can better detect DNA molecules when the sensors can view a greater thickness of fluid. Therefore, heat exchange chambers with greater chamber height or opening thickness can also be a beneficial location for optical sensors to detect DNA molecules in the fluid.

Figure 7:
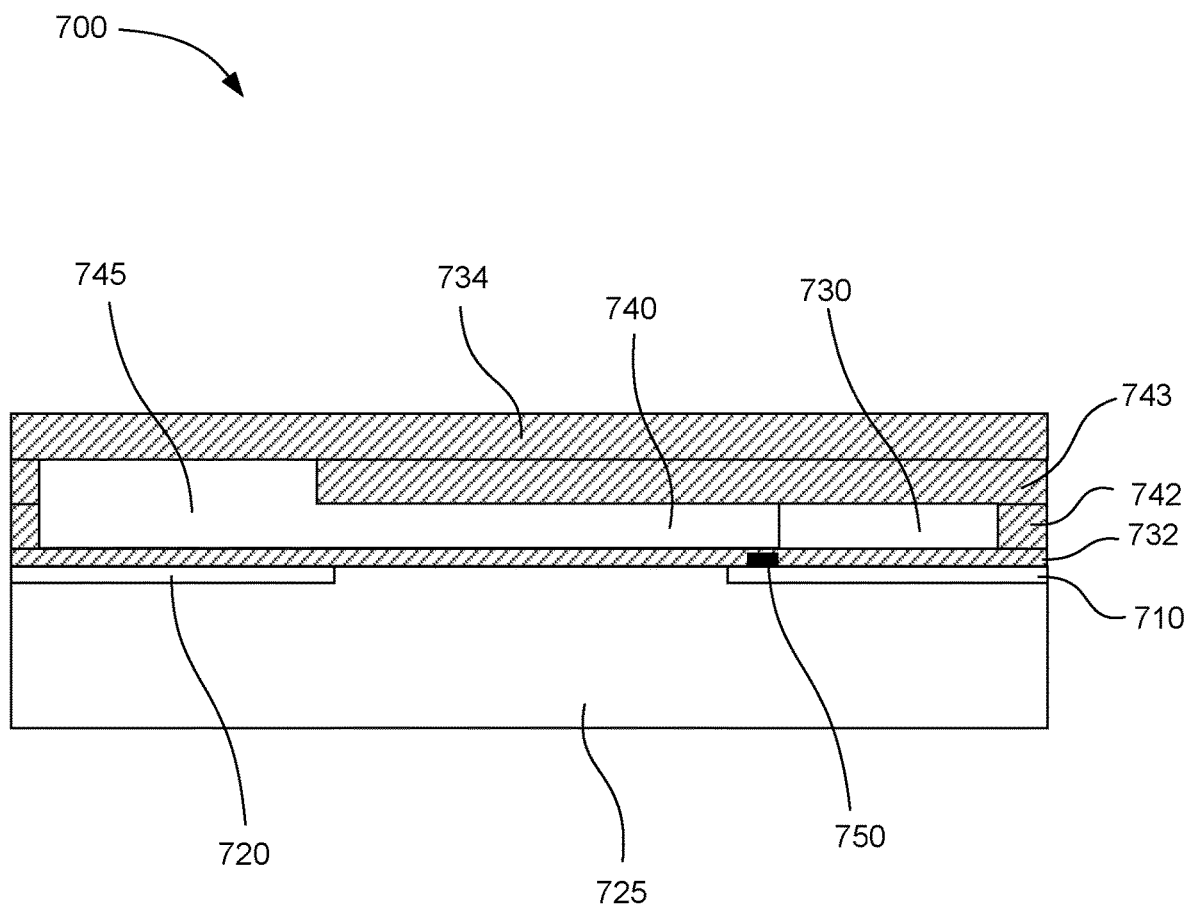
FIG. 7 is a side cross-sectional view of another example temperature-cycling microfluidic device in accordance with the present disclosure.

FIG. 7 shows a side cross-sectional view of an example temperature-cycling microfluidic device 700. This device has the same top-down appearance as the device shown in FIG. 6 and this device also includes heat exchange chambers 745 that have a greater chamber height than the remainder of the microfluidic loops 740. In this example, a driver chip 710 and heat exchange chip 720 are embedded at the surface of a substrate 725. Fluid actuators 750 are located on the surface of the driver chip. A thin floor layer 732 is formed over the chips and the substrate. A microfluidic layer 742 is the deposited over the floor layer to define a fluid chamber 730, microfluidic loops, and the heat exchange chambers. A second microfluidic layer 743 is then deposited that acts as the ceiling of the microfluidic loops and the fluid chamber, but that includes an opening to make the heat exchange chamber larger in height. Finally, a ceiling layer 734 is deposited over the second microfluidic layer. In further examples, the heat exchange chamber can be made even thicker or taller in height by adding additional layers of material or by using thicker layers of material. Additionally, the layered approach to constructing these microfluidic devices is only one example method of construction. Any other suitable method can also be used to make the microfluidic devices described herein.

In further examples, additional heat exchange chips can be added to provide more control over the temperature of the fluid in the microfluidic loops. In some examples, the driver chip and multiple heat exchange chips can all be held at different temperatures to facilitate chemical reactions that are favored by more than two temperature ranges. In certain examples, a PCR amplification test can be performed using a three-temperature cycle. In a specific example, the cycle can begin by holding the sample fluid at a high relative temperature of 90° C. to 100° C., then holding at a low relative temperature of 50° C. to 65° C., and then holding at an intermediate temperature of 70° C. to 82° C. These three temperatures can be repeated to multiply the DNA molecules. The high, low, and intermediate temperatures can correspond to denaturation, annealing, and elongation stages in the PCR reaction, respectively.

Figure 8:
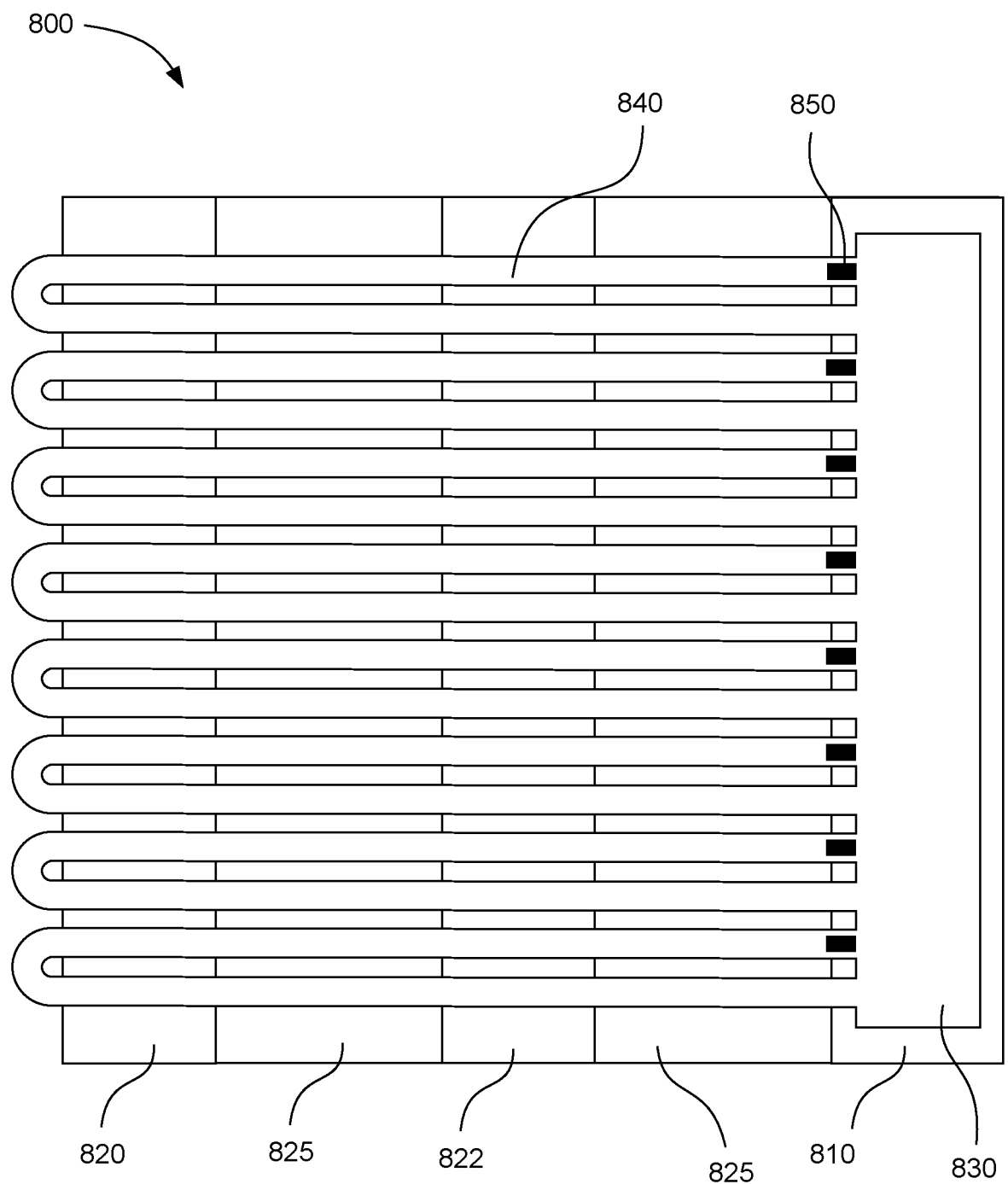
FIG. 8 is a schematic view of still another example temperature-cycling microfluidic device in accordance with the present disclosure.

FIG. 8 shows an example temperature-cycling microfluidic device 800 that includes a first heat exchange chip 820 and a second heat exchange chip 822. The heat exchange chips are separated from a driver chip 810 and one from another by a substrate 825. A fluid chamber 830 is located over the driver chip, and multiple microfluidic loops 840 connect to the fluid chamber. Multiple fluid actuators 850 are located at fluid driving ends of the microfluidic loops. The microfluidic loops extend across both the first and second heat exchange chips. In this example, the driver chip, first heat exchange chip, and second heat exchange chip can be held at a different temperature so that the fluid cycles between three independent temperatures.

As mentioned above, in some examples the microfluidic device can be used together with a reading device that connects to the microfluidic device through electrical interfaces. The reading device can perform a variety of functions, such as providing power to the fluid actuators, heaters, and sensors of the microfluidic device. In some examples the reading device can include a processor that can be configured to receive signals from the sensors of the microfluidic device and control the heaters and fluid actuators of the microfluidic device. The processors can also be programmed to maintain chips in the microfluidic device at specific temperatures. More complex programs can be used for performing specific procedures with the microfluidic device, such as a PCR amplification test. In some examples, such programs can be more complex than simply holding the chip temperatures at certain values. For example, a PCR program may include initiation operations, ramp up of temperature in the driver chip and heat exchange chip, controlling the pumping speed of the fluid actuators, performing a specific number of cycles of fluid through the microfluidic loops, detecting the presence of amplified DNA in the sample fluid, and a variety of other operations. Other functions that can be performed by the reading device can include storing data, displaying test results to a user, receiving manual inputs from a user to change parameters of the test being performed by the microfluidic device, and so on.

The form factor of the reading device is not particularly limited. In some examples, the reading device can be a personal computer with an interface for connecting to the microfluidic device. In other examples, the reading device can be a specialized handheld device, a mobile device such as a smartphone or tablet with an interface for connecting to the microfluidic device, and so on.

Figure 9:
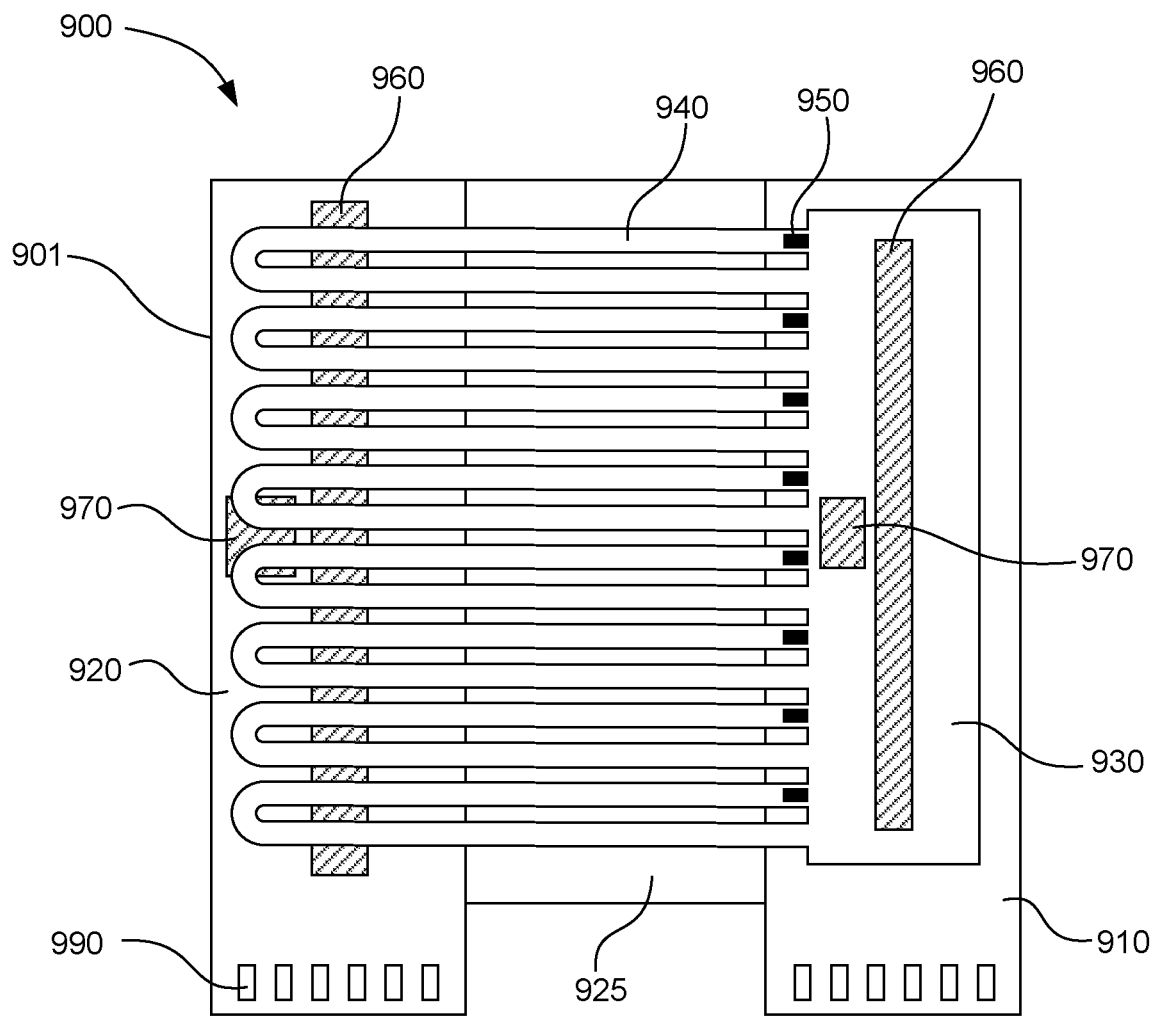
FIG. 9 is a schematic view of an example system for heating and cooling a fluid in accordance with the present disclosure.
Figure 9:
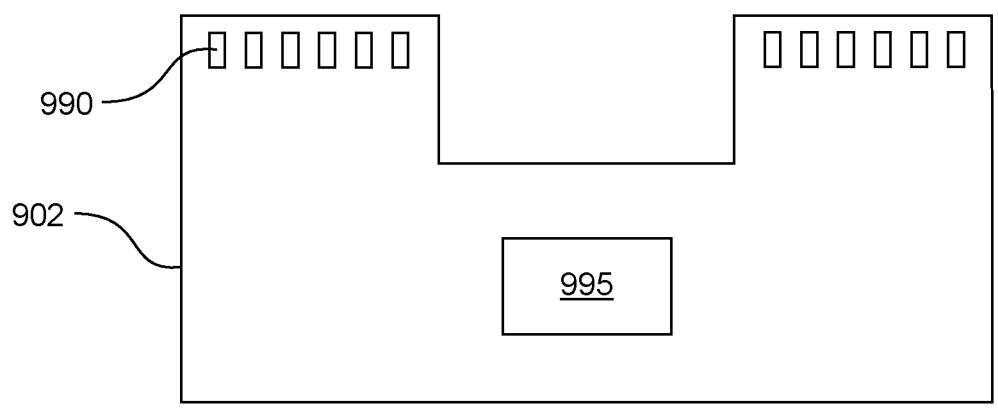

FIG. 9 shows an example system 900 for heating and cooling a fluid. The system includes a temperature-cycling microfluidic device 901 and a reading device 902. The microfluidic device includes a driver chip 910, a heat exchange chip 920 separated from the driver chip by substrate 925, a fluid chamber 930 over the driver chip, multiple microfluidic loops 940 connecting to the fluid chamber, and multiple fluid actuators 950 at fluid driving ends of the microfluidic loops to pump fluid through the microfluidic loops. The driver chip and the heat exchange chip include a heater 960 and a temperature sensor 970. The driver chip and heat exchange chip also include electrical interfaces 990 connected to the heaters and temperature sensors. The reading device includes electrical interfaces that can connect to the electrical interfaces of the driver chip and heat exchange chip. The reading device also includes a processor 995 to measure temperatures using the temperature sensors and control the temperatures using the heaters of the microfluidic device. The processor can also control the fluid actuators to pump fluid through the microfluidic loops. In some examples, the driver chip and heat exchange chip may not necessarily have their own separate electrical interfaces. Rather, the microfluidic device as a whole can be designed to have a single electrical interface that can plug into the reading device through a port, cable, or the like.

A variety of other configurations can be used with various numbers of driver chips and heat exchange chips. The chips can include a variety of different electronic components, such as fluid actuators, heaters, temperature sensors, DNA sensors, and so on. It should be understood that the figures and description above are not to be considered limiting unless otherwise stated. The microfluidic devices can include a variety of other components and features that are not depicted in the figures, such as capillary breaks, vents, valves, and any other suitable features.

As explained above, the microfluidic devices described herein can be used for a variety of application, especially applications involving mixing and repeatedly heating fluids to multiple temperatures. In some examples, the microfluidic devices can be used for PCR testing, which involves cycling the sample fluid between a high and low temperature many times.

In one example, the microfluidic devices described herein can be used to perform a method of heating and cooling a fluid. For example, a fluid sample can be loaded into a fluid chamber located over a driver chip. The fluid sample can then be driven from the fluid chamber into multiple microfluidic loops. Individual microfluidic loops can have a fluid driving end and a fluid outlet end connected to the fluid chamber, and the individual microfluidic loops include a portion thereof located over a heat exchange chip that is coplanar with the driver chip and separated from the driver chip by a substrate having a lower thermal conductivity than the heat exchange chip. The driver chip can be maintained at a first temperature and the heat exchange chip can be maintained at a second temperature.

In the particular case of PCR DNA testing, the microfluidic device can be loaded with a fluid to be tested for DNA in the fluid chamber. The driver chip under the fluid chamber can be held at a high relative temperature to denature the nucleic acid. The heat exchange chip can be held at a low relative temperature to anneal primers to the denatured nucleic acids and to synthesize new nucleic acid strands. In certain examples, target temperature for the fluid in the high relative temperature range can be from 80° C. to 103° C., and the target temperature for the fluid in the low relative temperature range can be from 48° C. to 82° C. Accordingly, the driver chip can be maintained at a temperature slightly above the target high temperature and the heat exchange chip can be held at a temperature slightly below the target low temperature as explained above. The fluid can be circulated through the microfluidic loops, so that the fluid completes a temperature cycle from the high relative temperature to the low relative temperature and back every time the fluid cycles around a loop. In some examples, the fluid can complete a temperature cycle in a time from 5 milliseconds to 15 seconds, depending on the rate of pumping and the length of the microfluidic loops.

In some examples, a three-temperature cycle can be used. The cycle can begin by heating the sample fluid in the fluid chamber to a high relative temperature of 90° C. to 100° C., then cooling to a low relative temperature of 50° C. to 65° C., and then heating to an intermediate temperature of 70° C. to 82° C. These three temperatures can be repeated to multiply the DNA molecules. The high, low, and intermediate temperatures can correspond to denaturation, annealing, and elongation stages in the PCR reaction, respectively.

In further examples, the heat exchange chip can be held at a high relative temperature and the driver chip can be held at a low relative temperature. Any of the features of the microfluidic devices described above can be used to perform specific methods of heating and cooling fluids. As explained above, the microfluidic loops can have a variety of features such as multiple turns, heat exchange chambers with a greater chamber height than the microfluidic loops, and so on in order to more precisely control the temperature of the fluids flowing through the microfluidic loops.

In one specific example, a microfluidic device is constructed similar to the design shown in FIGS. 3A-3B. The driver chip is formed of silicon with thermal resistors formed thereon to be used as fluid actuators. A resistive heater, temperature sensor, and DNA sensor are also formed on the heat exchange chip. The driver chip also includes a heater and temperature sensor for temperature control of the driver chip. The substrate surrounding the driver chip is SU-8 epoxy. A thin layer of SU-8 photoresist is coated over the driver chip as a floor for the fluid chamber and microfluidic loops. Another layer of SU-8 is then deposited and patterned by exposing the layer to UV light in the pattern of the walls of the microfluidic loops and the fluid chamber. Uncured SU-8 is then removed to form the fluid chamber and microfluidic loops. A ceiling is then deposited over the fluid chamber and microfluidic loops by dry laminating a photoresist layer over the microfluidic layer. The ceiling is patterned to leave an aperture open for filling the fluid chamber. The ceiling is then developed by removed uncured photoresist.

In a further specific example, a sample fluid is filled into the fluid chamber of the microfluidic device. The sample fluid contains at least one DNA molecule to be amplified and a mixture of primers, bases, and polymerase for carrying out the amplification reactions. The microfluidic device is connected to a separate reader device through the electronic interface on the driver chip. The reader device includes electronics for power the fluid actuators, heaters, temperature sensors, and DNA sensor on the driver chip. The reader device activates the fluid actuators at a frequency of 2 kHz to 30 kHz. to circulate sample fluid through the microfluidic loops. The reader performs a PCR amplification program by maintaining the fluid in the fluid chamber at a high temperature of 95° C. to denature DNA in the fluid and maintaining the temperature of the fluid passing over the heat exchange chip at a low temperature of 60° C. to anneal primers to the denatured single stranded DNA molecules. The fluid is circulated through the microfluidic loops until the DNA sensor detects the amplified DNA molecules in the sample fluid.

It is to be understood that this disclosure is not limited to the particular process steps and materials disclosed herein because such process steps and materials may vary somewhat. It is also to be understood that the terminology used herein is used for the purpose of describing particular examples only. The terms are not intended to be limiting because the scope of the present disclosure is intended to be limited only by the appended claims and equivalents thereof.

It is noted that, as used in this specification and the appended claims, the singular forms "a," "an," and "the" include plural referents unless the context clearly dictates otherwise.

As used herein, the term "substantial" or "substantially" when used in reference to a quantity or amount of a material, or a specific characteristic thereof, refers to an amount that is sufficient to provide an effect that the material or characteristic was intended to provide. The exact degree of deviation allowable may in some cases depend on the specific context.

As used herein, the term "about" is used to provide flexibility to a numerical range endpoint by providing that a given value may be "a little above" or "a little below" the endpoint. The degree of flexibility of this term can be dictated by the particular variable and determined based on the associated description herein.

As used herein, multiple items, structural elements, compositional elements, and/or materials may be presented in a common list for convenience. However, these lists should be construed as though the members of the list are individually identified as a separate and unique member. Thus, no individual member of such list should be construed as a de facto equivalent of any other member of the same list solely based on their presentation in a common group without indications to the contrary.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include individual numerical values or sub-ranges encompassed within that range as if various numerical value and sub-range is explicitly recited. As an illustration, a numerical range of "about 1 wt % to about 5 wt %" should be interpreted to include not only the explicitly recited values of about 1 wt % to about 5 wt %, but also include individual values and sub-ranges within the indicated range. Thus, included in this numerical range are individual values such as 2, 3.5, and 4 and sub-ranges such as from 1-3, from 2-4, and from 3-5, etc. This same principle applies to ranges reciting only one numerical value. Furthermore, such an interpretation should apply regardless of the breadth of the range or the characteristics being described.

What is claimed is:

1. A temperature-cycling microfluidic device, comprising:
   a driver chip having a top surface;
   a heat exchange substrate having a top surface coplanar with the top surface of the driver chip;
   a fluid chamber located on the top surface of the driver chip;
   a first microfluidic loop having a fluid driving end and a fluid outlet end connected to the fluid chamber, wherein the first microfluidic loop includes a portion thereof located on the top surface of the heat exchange substrate;
   a first fluid actuator on the driver chip associated with the fluid driving end of the first microfluidic loop to circulate fluid through the first microfluidic loop;
   a second microfluidic loop having a fluid driving end and a fluid outlet end connected to the fluid chamber, wherein the second microfluidic loop includes a portion thereof located on the top surface of the heat exchange substrate; and
   a second fluid actuator on the driver chip associated with the fluid driving end of the second microfluidic loop to circulate fluid through the second microfluidic loop.

2. The microfluidic device of claim 1, wherein the heat exchange substrate is a heat exchange chip comprising silicon.

3. The microfluidic device of claim 2, wherein the heat exchange chip is separated from the driver chip by a substrate having a lower thermal conductivity than the heat exchange chip.

4. The microfluidic device of claim 2, wherein the heat exchange chip is to cool the fluid to a temperature lower than a temperature of the fluid chamber.

5. The microfluidic device of claim 4, further comprising an intermediate chip located between the driver chip and the heat exchange chip, the intermediate chip to heat the fluid to an intermediate temperature between the temperature of the heat exchange chip and the temperature of the fluid chamber.

6. The microfluidic device of claim 2, wherein the heat exchange chip comprises a heater, a temperature sensor, a nucleic acid sensor, or a combination thereof.

7. The microfluidic device of claim 1, wherein the driver chip further comprises a heater, a temperature sensor, a nucleic acid sensor, or a combination thereof.

8. The microfluidic device of claim 1, wherein the first and second microfluidic loops comprise multiple turns over the heat exchange substrate.

9. The microfluidic device of claim 1, wherein the fluid actuators are thermal resistors or piezoelectric elements.

10. A temperature-cycling microfluidic device, comprising:
   a driver chip having a top surface;
   a heat exchange chip having a top surface coplanar with the top surface of the driver chip;
   a fluid chamber located on the top surface of the driver chip;
   a first microfluidic loop having a fluid driving end and a fluid outlet end connected to the fluid chamber, wherein the first microfluidic loop includes a first heat exchange chamber over the heat exchange chip, wherein the first heat exchange chamber has a greater chamber height than a remainder of the first microfluidic loop;
   a first fluid actuator on the driver chip associated with the fluid driving end of the first microfluidic loop to circulate fluid through the first microfluidic loop;
   a second microfluidic loop having a fluid driving end and a fluid outlet end connected to the fluid chamber, wherein the second microfluidic loop includes a second heat exchange chamber over the heat exchange chip, wherein the second heat exchange chamber has a greater chamber height than a remainder of the second microfluidic loop; and
   a second fluid actuator on the driver chip associated with the fluid driving end of the second microfluidic loop to circulate fluid through the second microfluidic loop.

11. The microfluidic device of claim 10, wherein the first microfluidic loop includes an additional heat exchange chamber over the driver chip, and wherein the second microfluidic loop includes an additional heat exchange chamber over the driver chip.

12. A system for heating and cooling a fluid, comprising:
   a temperature-cycling microfluidic device, including:
      a driver chip comprising a temperature sensor, a heater, and an electrical interface electrically connected to the temperature sensor and heater,
      a heat exchange chip coplanar with the driver chip and separated from the driver chip by a substrate, wherein the heat exchange chip comprises a temperature sensor, a heater, and an electrical interface electrically connected to the temperature sensor and heater,
      a fluid chamber located over the driver chip,
      multiple microfluidic loops, wherein individual microfluidic loops have a fluid driving end and a fluid outlet end connected to the fluid chamber, and wherein the individual microfluidic loops include a portion thereof located on the heat exchange chip, and
      multiple fluid actuators on the driver chip, wherein individual fluid actuators are associated with the fluid driving end of individual microfluidic loops to circulate fluid through the microfluidic loops; and
   a reading device comprising electrical interfaces to connect to the electrical interfaces of the driver chip and the heat exchange chip, wherein the reading device includes a processor to drive the fluid actuators, measure temperatures using the temperature sensors, and heat the driver chip and heat exchange chip to control the temperature of the chips within a temperature range.

13. The system of claim 12, wherein the heat exchange chip is to cool the fluid to a lower temperature than the driver chip.

14. The system of claim 12, wherein the substrate has a lower thermal conductivity than the heat exchange chip.

15. The system of claim 12, wherein the microfluidic device further comprises an intermediate chip located between the driver chip and the heat exchange chip, the intermediate chip being to heat the fluid to an intermediate temperature between the temperature of the heat exchange chip and the temperature of the fluid chamber.

* * * * *